United States Patent [19]

O'Neil

[11] Patent Number: 5,171,463
[45] Date of Patent: Dec. 15, 1992

[54] N-SUBSTITUTED TRIAZOLE COMPOUNDS

[75] Inventor: Robert M. O'Neil, Manchester, England

[73] Assignee: Ciba-Geigy Corporation, Ardsley, N.Y.

[21] Appl. No.: 845,519

[22] Filed: Feb. 27, 1992

Related U.S. Application Data

[63] Continuation of Ser. No. 725,380, Jun. 27, 1991, abandoned, which is a continuation of Ser. No. 549,526, Jul. 6, 1990, abandoned.

[30] Foreign Application Priority Data

Jul. 14, 1989 [GB] United Kingdom ................ 8916195

[51] Int. Cl.$^5$ ............................................ C10M 145/06
[52] U.S. Cl. .............................. 252/47.5; 252/51.5 A; 252/51.5 R; 548/267.8
[58] Field of Search ............ 252/47.5, 51.5 A, 51.5 R; 548/267.8

[56] References Cited

U.S. PATENT DOCUMENTS

| | | | |
|---|---|---|---|
| 4,153,565 | 5/1979 | Braid et al. | 252/51.5 |
| 4,260,501 | 4/1981 | Shim | 252/47.5 |
| 4,507,140 | 3/1985 | Sugavanam | 548/267.8 |
| 4,946,493 | 8/1990 | Sugavanam | 548/267.8 |

FOREIGN PATENT DOCUMENTS

| | | |
|---|---|---|
| 0365476 | 4/1990 | European Pat. Off. . |
| 2002772 | 2/1979 | United Kingdom . |
| 1563199 | 3/1980 | United Kingdom . |

Primary Examiner—Olik Chaudhuri
Assistant Examiner—M. Nuzzolillo
Attorney, Agent, or Firm—Luther A. R. Hall

[57] ABSTRACT

New triazole compounds, useful as metal deactivators and/or antioxidants in organic material, having the formula I:

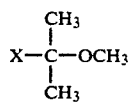

(I)

wherein X is the triazole residue of formula II:

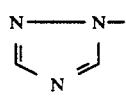

(II)

or the benzotriazole residue of formula III or IIIA:

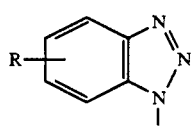

(III)

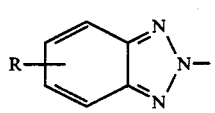

(IIIA)

in which R is hydrogen or methyl.

10 Claims, No Drawings

N-SUBSTITUTED TRIAZOLE COMPOUNDS

This is a continuation of application Ser. No. 725,380, filed on Jun. 27, 1991, now abandoned, which is in turn a continuation of application Ser. No. 549,526, filed on Jul. 6, 1990, now abandoned.

The present invention relates to new triazole compounds, to their production and to their use as metal deactivators and/or antioxidants in organic material such as mineral oils.

In British Patent Specification No. 2002772, there are described compounds, useful as metal deactivators in lubricants, and having the formula:

[structure: benzotriazole-N-CH$_2$-OR$_1$]

wherein R$_1$ is 1-18C alkyl, 3-18C alkyl, 5-12C cycloalkyl or 6-10C aryl, each optionally substituted with one or more 1-2C alkyl or 7-9C alkyl groups.

U.S. Pat. No. 4,153,565 discloses lubricant compositions containing, as antioxidants and corrosion inhibitors, the adduct of i) benzotriazole, optionally ring-substituted with a 1-12C hydrocarbyl group, and ii) an alkyl vinyl ether or a vinyl ester of a hydrocarbylcarboxylic acid for formula $$R_{II}-CH=CH-O-R_{III}$$

$$R_{II}-CH=CH-O-C(=O)-R_{IV}$$

in which $R_{II}$ is hydrogen or a 1-8C alkyl group, $R_{III}$ is 1-18C alkyl and $R_{IV}$ is alkyl, aryl, alkaryl or aralkyl containing 1-18C atoms.

Also known, in U.S. Pat. No. 4,260,501, are lubricant compositions comprising the adducts of U.S. Pat. No. 4,153,565 together with an alkyl dimercapto thiadiazole, especially tertiary octyl 2,5-dimercapto thiadiazole, more especially tertiary octyl 2,5-dimercapto-1,3,4-thiadiazole.

We have now found that certain N-substituted triazoles provide improved metal deactivator and antioxidant properties when incorporated into organic material e.g. mineral oils.

Accordingly, the present invention provides new triazole compounds having the formula I:

$$X-\underset{\underset{CH_3}{|}}{\overset{\overset{CH_3}{|}}{C}}-OCH_3 \quad (I)$$

wherein X is the triazole residue of formula II:

[structure II: triazole ring N—N—, N]

or the benzotriazole residue of formula III or IIIA:

[structure III: benzotriazole with R substituent]

[structure IIIA: benzotriazole with R substituent]

in which R is hydrogen or methyl.

The compounds of formula I may be produced by reacting, in the presence of an acid catalyst, 2-methoxypropene of formula IV:

$$\underset{\underset{CH_3}{|}}{\overset{\overset{CH_2}{\|}}{C}}-OCH_3 \quad (IV)$$

with a triazole compound having the formula V, VI or VIA:

[structures V, VI, VIA]

in which R has its previous significance.

Due to the tautomerism between formulae VI and VIA, two possible products may be obtained, represented by formulae III and IIIA, respectively.

The process is conveniently performed in an inert solvent, at ambient or elevated temperature. Solvents which may be used include aromatic solvents such as benzene, toluene or xylene; cyclohexane; carbon tetrachloride; or dioxan.

The amount of 2-methoxypropene reactant of formula IV used is preferably that which is stoichiometrically required for complete reaction with the triazole compound of formula V or VI, or a slight excess over the stoichiometric amount required. Preferably 1-10%, especially 5-10% molar excess of 2-methoxypropene is used relative to the triazole component.

Acid catalysts for use in the process include e.g. sulphuric acid, phosphoric acid, an acid ion-exchange resin, e.g. Amberlyst 15, bentonite, montmorillonite, Fuller's earth or p-toluene sulphonic acid.

Most preferably, the reaction may be effected by the dropwise addition of 2-methoxypropene to a solution of the triazole compound of formula V or VI, dissolved in toluene or dioxan, at 25° to 60° C., in the presence of a catalytic amount of p-toluene sulphonic acid, preferably 1-10 weight %, especially 1-5 weight %, based on the triazole component.

The product of formula I may be isolated from the reaction mixture by removal of catalyst and reaction solvent, followed by vacuum distillation of the residue.

According to the present invention, there is also provided a composition comprising an organic material and, as metal deactivator and/or antioxidant, at least one compound having the formula I, as hereinbefore defined.

The organic material component of the compositions of the present invention may be any organic material which is susceptible to degradation in the presence of degradants such as metals and/or oxygen. Examples of such organic materials are mineral oils, synthetic oils, plastics or other polymers.

Of particular interest are lubricants which are of mineral oil origin or are synthetic oils e.g. carboxylic acid esters, especially those intended for use at temperatures at or above 200° C.

Examples of carboxylic acid ester synthetic lubricants include those based on a diester of a dibasic acid and a monohydric alcohol e.g. dioctyl sebacate or dinonyl adipate; or a triester of trimethylol propane and a monobasic acid or mixture of such acids e.g. trimethylol propane tripelargonate, trimethylol propane tricaprylate or mixtures of these; on a tetraester of pentaerythritol and a monobasic acid or a mixture of such acids e.g. pentaerythritol tetracaprylate; or on complex esters derived from monobasic acids, dibasic acids and polyhydric alcohols e.g. a complex ester derived from trimethylolpropane, caprylic acid and sebacic acid; or mixtures of one or more of such carboxylic acid esters.

Other synthetic lubricant bases are those described e.g. in "Schmiermmittel-Taschenbuch" (Huethig Verlag, Heidelberg 1974), e.g. phosphates, glycols, polyglycols, polyalkylene glycols and poly-alpha olefins.

Mineral oil-based lubricant bases are preferred.

The compositions of the present invention preferably contain 0.001 to 5.0%, more preferably 0.02 to 1.0% by weight of a compound of formula I, based on the weight of the organic material.

In addition to the compound of formula I, the organic material compositions according to the present invention may contain, in order to improve the operating properties of the organic material, further additives. Such further additives include, in the case of preferred lubricant organic materials, e.g. further antioxidants e.g. phenolic antioxidants, amine antioxidants, or other antioxidants, further metal deactivators, rust inhibitors, viscosity-index improvers, pour-point depressants, dispersants/-surfactants, and anti-wear additives.

The compounds of formula I, when used alone, exert an excellent metal deactivating effect on working metal surfaces e.g. engine parts, especially of iron or, in particular copper, in contact with an organic material containing a metal degradant such as sulphur.

When, however, the organic material per se is the primary target for degradation e.g. when used in the presence of adventitious traces of metals such as iron or copper, and/or oxygen and/or hydroperoxides, then it is very much preferred to use the compound of formula I in combination with a further antioxidant.

EXAMPLES OF PHENOLIC ANTIOXIDANTS

1. Alkylated Monophenols 2,6-Di-tert-butyl-4-methylphenol, 2,6-di-tert-butylphenol, 2-tert-butyl-4,6-dimethylphenol, 2,6-di-tert-butyl-4-ethylphenol, 2,6-di-tert-butyl-4-n-butylphenol, 2,6-di-tert-butyl-4i-butylphenol, 2,6-di-cyclopentyl-4-methylphenol, 2(β-methylcyclohexyl)-4,6-di-methylphenol, 2,6-di-octadecyl-4-methylphenol, 2,4,6-tricyclohexylphenol, 2,6-di-tert-butyl-4-methoxymethylphenol, o-tert-butylphenol.

2. Alkylated Hydroquinones 2,6-Di-tert-butyl-4-methoxyphenol, 2,5-di-tert-butylhydroquinone, 2,5di-tert-amylhydroquinone, 2,6-diphenyl-4-octadecyloxyphenol.

3. Hydroxylated Thiodiphenylethers 2,2'-Thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)-phenol), 2,2'-methylene-bis-(4,6-di-tert-butyl-phenol), 2,2'-ethylidene-bis-(4,6-di-tert-butylphenol), 2,2'-ethylidene-bis-(6-tert-butyl-4-or-5-isobutylphenol), 2,2'-methylene-bis(6-α-methylbenzyl-4-nonylphenol), 2,2'-methylene-bis-(6-(α,α-dimethylbenzyl)-4-nonylphenol), 4,4'-methylene-bis-(2,6-di-tert-butylphenol), 4,4'-methylene-bis(6-tert-butyl-2-methylphenol), 1,1'-bis-(5-tert-butyl-4-hydroxy-2-methylphenol)-butane, 2,6-di-(3-tert-butyl-5-methyl-2-hydroxybenzyl)-4-methylphenol, 1,1,3-tris-(5-tert-butyl-4-hydroxy-2-methylphenyl)-3-n-dodecyl)-mercapto-butane, ethyleneglycol-bis-[3,3-bis-(3'-tert-butyl-4'-hydroxyphenyl)-butyrate], bis-(3-tert-butyl-4-hydroxy-5-methylphenyl)-dicyclo-pentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-tri-methyl-benzene, bis-(3,5di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethylbenzyl)-dithiolterephthalate, 1,3,5-tris-(3,5-di-tert-butyl-4-hydroxy-benzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxy-benzyl-phosphonic acid-monoethylester, calcium-salt.

6. Acylaminophenols

4-Hydroxy-lauric acid analide, 4-hydroxy-stearic acid analide, 2,4-bis-octylmercapto-6-(3-,5-di-tert-butyl-4-hydroxy-anilino)-s-triazine, N-(3,5-di-tert-butyl-4-hydroxyphenyl)-carbamic acid octyl ester.

7. Esters of β-(3,5-Di-tert-butyl-4-hydroxyphenol)-propionic acid with mono- or polyhydric alcohols, for example with methanol, diethyleneglycol, octadecanol, triethyleneglycol, 1,6-hexanediol, pentaerythritol, neopentylglycol, tris-hydroxyethyl-isocyanurate, thiodiethyleneglycol, bis-hydroxyethyl-oxalic acid diamide.

8. Esters of β-(5-tert-butyl-4-hydroxy-3-methylphenyl)-propionic acid with mono- or polyhydric alcohols, for example with methanol, diethyleneglycol, octadecanol, triethyleneglycol, 1,6-hexanediol, pentaerythritol, neopentylglycol, tris-hydroxyethyl-isocyanurate, thiodiethyleneglycol, di-hydroxyethyl-oxalic acid diamide.

9. Amides of
β-(3,5-Di-tert-butyl-4-hydroxyphenyl)-propionic acid for example

N,N'-Bis-(3,5-di-tert-butyl-4-hydroxyphenylpropionyl)-hexamethyl-enediamine, N,N'-bis-(3,5-di-tert-butyl-4-hydroxyphenyl-propionyl)-trimethylene-diamine, N,N'-bis-(3,5-di-tert-butyl-4-hydroxyphenylpropionyl)-hydrazine.

EXAMPLES OF AMINE ANTIOXIDANTS

N,N'-Di-isopropyl-p-phenylenediamine, N,N'-di-sec.-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethyl-butyl)-N'-phenyl-p-phenylene-diamine, N-(1-methylheptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-phenyl-2-naphthyl-amine, octylated diphenylamine, e.g. p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, di-(4-methoxy-phenyl)-amine, 2,6-di-tert-butyl-4-dimethylamino-methylphenol, 2,4'-diamino-diphenylmethane, 4,4'-diamino-diphenylmethane, N,N,N',N'-tetramethyl-4,4'-diamino-diphenylmethane, 1,2-di-(phenylamino)-ethane, 1,2-di-[2-methyl-phenyl)-amino]-ethane, 1,3-di-(phenyl-amino)-propane, (o-tolyl)-biguanide, di-[4-(1',3'-dimethylbutyl)-phenyl]amine, tert-octylated N-phenyl-1-naphthyl-amine, mixture of mono- and dialkylated tert-butyl-/tert-octyldiphenylamines, 2,3-dihydro-3,3-dimethyl-4H-1,4-benzothiazine, phenothiazine, n-allylphenothiazine.

EXAMPLES FOR OTHER ANTIOXIDANTS

Aliphatic or aromatic phosphites, esters of thiodipropionic acid or of thiodiacetic acid, or salts of dithiocarbamic or dithiophosphoric acid.

EXAMPLES OF METAL DEACTIVATORS, FOR EXAMPLE FOR COPPER, ARE

Triazoles, benzotriazoles and derivatives thereof, tolutriazole and derivatives thereof, 2-mercaptobenzothiazole, 2,5-dimercaptothiadiazole, 5,5'-methylene-bis-benzotriazole, 4,5,6,7-tetrahydro-benzotriazole, salicylidene-propylenediamine and salicylaminoguanidine and salts thereof.

EXAMPLES OF RUST INHIBITORS ARE a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amides, 4-nonylphenoxy-acetic acid.

b) Nitrogen-containing compounds, e.g. I Primary, secondary or tertiary aliphatic or cycloaliphatic amines and amine-salts of organic and inorganic acids, e.g. oil-soluble alkylammonium carboxylates II Heterocyclic compounds, e.g. substituted imidazolines and oxazolines.

c) Phosphorus-containing compounds, e.g. Amine salts of phosphonic acid or phosphoric acid partial esters, zinc dialkyldithio phosphates.

d) Sulphur-containing compounds, e.g. Barium-dinonylnaphthalene-n-sulphonates, calcium petroleum sulphonates.

EXAMPLES OF VISCOSITY-INDEX IMPROVERS ARE

Polyacrylates, polymethacrylates, vinylpyrrolidone/methacrylate-co-polymers, polyvinylpyrrolidones, polybutenes, olefin-copolymers, styrene/acrylate-copolymers, polyethers.

EXAMPLES OF POUR-POINT DEPRESSANTS ARE

Polymethacrylates, alkylated naphthalene derivatives.

EXAMPLES OF DISPERSANTS/SURFACTANTS ARE

Polybutenylsuccinic acid-amides or -imides, polybutenylphosphonic acid derivatives, basic magnesium-, calcium-, and barium-sulfonates and -phenolates.

EXAMPLES OF ANTI-WEAR ADDITIVES ARE

Sulphur- and/or phosphorus- and/or halogen-containing compounds e.g. sulphurised vegetable oils, zinc dialkyldithio-phosphates, tritolyl-phosphate, chlorinated paraffins, alkyl- and aryldi- and tri-sulphides, triphenylphosphorothionate.

When the organic material is an organic material liable to degradation by oxidation, e.g. a lubricant composition, one particular preferred class of co-additives for use in conjunction with the compounds of formula I, comprises phenolic or amine-type antioxidants, especially amine-type antioxidants e.g. diphenylamine, octylated diphenylamine, N-phenyl-1-naphthylamine and N-(octylated-phenyl)-1-naphthyl-amine, with which the compounds of formula I exhibit a synergistic effect.

The following Examples further illustrate the present invention.

EXAMPLE 1

2-[1H-Benzotriazolyl]-2'-methoxypropane

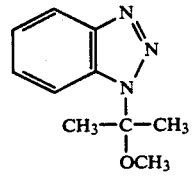

A solution of benzotriazole (23.8 g; 0.20 mole) in toluene (200 ml) containing p-toluene sulphonic acid (0.24 g) is maintained at 60° C. and treated, dropwise, over 30 minutes with 2-methoxypropene (15.8 g/ 0.22 mole). After complete addition, the mixture is maintained at 60° C. for a further 30 minutes. The mixture is allowed to cool to ambient temperature, washed with dilute sodium carbonate solution, then with water and, finally, dried over anhydrous magnesium sulphate. The dried extract is filtered and evaporated to dryness on a rotary evaporator to yield the crude product as a pale yellow oil (31.7 g; 83%). The pure product is obtained as a colourless oil by vacuum distillation, bp 113°/30 Pa.

Analysis: Found C 62.29%; H 6.74%; N 22.33%
$C_{10}H_{13}N_3O$ Requires C 62.81%; H 6.85%; N 21.97%.

EXAMPLE 2

2-[1H-Tolyltriazolyl]-2'-methoxypropane

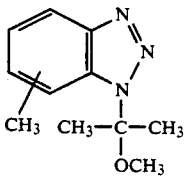

A solution of tolyltriazole (26.6 g; 0.2 mole) in toluene (200 ml) containing p-toluene sulphonic acid (0.27 g) is maintained at 25°–35° C. whilst being treated, dropwise, over 30 minutes with 2-methoxypropene (15.8 g; 0.22 mole). After complete addition, the mixture is heated to 60° C. and maintained at this temperature for 5 minutes. The mixture is allowed to cool to room temperature, washed with dilute sodium carbonate solution, then with water and, finally, dried over anhydrous magnesium sulphate. The dried extract is filtered and evaporated to dryness to yield the crude product as a pale yellow oil (37.1 g/ 93%). The pure product is obtained as a pale yellow oil by vacuum distillation, bp 120°/30 Pa.

Analysis: Found C 64.02%; H 7.69%; N 20.66%
$C_{11}H_{15}N_3O$ Requires C 64.36%; H 7.37%; N 20.48%

EXAMPLE 3

2-[1H-1,2,4-Triazolyl]-2'-methoxypropane

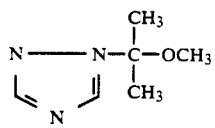

A solution of 1,2,4-triazole (6.9 g; 0.1 mole) in dioxan (200 ml) containing p-toluene sulphonic acid (0.20 g) is maintained at 50° C. and treated, dropwise, over 15 minutes with 2-methoxypropene (7.9 g; 0.11 mole). After complete addition, the mixture is heated to 100° C. and maintained at this temperature for 15 minutes. The mixture is allowed to cool ambient temperature and is then evaporated on a rotary evaporator. The oily product thus obtained is then extracted into ether and the extract washed with dilute sodium carbonate solution. The extract is dried over anhydrous magnesium sulphate and then filtered and evaporated to dryness on a rotary evaporator to yield the crude product as a pale yellow oil (11.7 g/ 79%). The pure product is obtained as a colourless oil by vacuum distillation, bp 60°/100 Pa.

Analysis: Found C 50.06%; H 7.86%; N 29.78%
$C_6H_{11}N_3O$ Requires C 51.05%; H 7.85%; N 29.78%.

EXAMPLES 4 TO 6

(Modified) ASTM D-130 Copper Strip Test

A 0.05% solution of the test compound is prepared in a turbine quality mineral oil of viscosity 26.2 mm²/s at 40° C., 4.8 mm²/s at 100° C. and S-content of 0.54% in which 50 ppm of elemental sulphur has been dissolved.

A copper strip (60×10×1 mm) is polished with 100 grade silicon carbide grit which has been picked upon on cotton wool wetted with petroleum ether. The polished strip is then immediately totally immersed in the prepared solution, which is maintained at 100° C. for 2 hours. After this time, the strip is removed, washed with petroleum ether, dried and its colour is compared with those of the ASTM D130 Copper Strip Standard Chart.

The results are summarised in the following Table:

| Modified ASTM D-130 Copper Strip Test | | |
|---|---|---|
| Example | Test compound | ASTM D-130 Rating |
| — | none (control) | 3B |
| 4 | Product Ex. 1 | 1A |
| 5 | Product Ex. 2 | 1A |
| 6 | Product Ex. 3 | 3B |

A rating of 1 denotes a slight tarnish; a rating of 2 a moderate tarnish; a rating of 3 a dark tarnish; and a rating of 4 severe corrosion. Letters A, B, C and D are used to indicate shadings within the broad numerical values. The results in the Table demonstrate the excellent test results achieved using compositions according to the present invention.

EXAMPLES 7 TO 12

Rotary Bomb Oxidation Test ASTM D-2272

A 0.05% solution of the test compound is prepared in a turbine quality mineral oil of viscosity 26.2 mm²/s at 40° C. 4.8 mm²s at 100° C. and S-content of 0.54% which may also contain either a phenolic or aminic antioxidant, or both.

The time taken for the oxygen pressure in the bomb to drop more than 175 kPa below the maximum pressure is recorded.

The results obtained are set out in the following Table:

| Example | Test Compound Product of Example No. | Antioxidant A | Antioxidant B | RBOT mins to 175 kPa pressure drop |
|---|---|---|---|---|
| control | Base oil alone | | | 25 mins |
| control | none | 0.10% | — | 65 mins |
| control | none | — | 0.10% | 85 mins |
| 7 | 1 | 0.10% | — | 540 mins |
| 8 | 1 | — | 0.10% | 310 mins |
| 9 | 2 | 0.10% | — | 415 mins |
| 10 | 2 | — | 0.10% | 555 mins |
| 11 | 3 | 0.10% | — | 420 mins |
| 12 | 3 | — | 0.10% | 1295 mins |

Antioxidant A is a commercially available mixture of tert-butylated phenols.

Antioxidant B is a commercially available di-tert-octylated diphenylamine.

The results in the Table indicate that, when used in combination with a further amine or phenolic antioxidant, the compounds of formula I impart synergistic antioxidant properties to the lubricant compositions of the invention.

I claim:

1. A triazole compound having the formula I

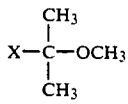

wherein X is the benzotriazole residue of formula III or IIIA

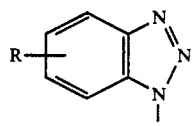

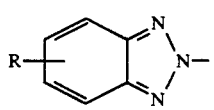

in which R is hydrogen or methyl.

2. A composition comprising a lubricant and an effective metal deactivating or antioxidant amount of at least one compound having the formula I, as defined in claim 1.

3. A composition according to claim 2 wherein the lubricant is a mineral oil or a synthetic oil.

4. A composition according to claim 3 wherein the lubricant is a mineral oil.

5. A composition according to claim 2 wherein 0.001 to 5.0% by weight of a compound of formula I is present, based on the weight of the lubricant.

6. A composition according to claim 5 wherein 0.02 to 1.0% by weight of a compound of formula I is present, based on the weight of the lubricant.

7. A composition according to claim 2 comprising one or more further additives known to improve the operating properties of the lubricant.

8. A composition according to claim 7 wherein the further additive is one or more of a further antioxidant, a further metal deactivator, a rust inhibitor, a viscosity-index improver, a pour-point depressant, a dispersant-/surfactant and an anti-wear additive.

9. A composition according to claim 8 wherein the further additive comprises a phenolic or amine-type antioxidant.

10. A composition according to claim 9 wherein the further additive is diphenylamine, octylated diphenylamine, N-phenyl-1-naphthylamine or N-(octylatedphenyl)-1-naphthylamine.

* * * * *